US005958893A

United States Patent [19]
Welsh et al.

[11] Patent Number: 5,958,893
[45] Date of Patent: *Sep. 28, 1999

[54] GENES AND PROTEINS FOR TREATING CYSTIC FIBROSIS

[75] Inventors: Michael J. Welsh, Riverside; David N. Sheppard, Coralville, both of Iowa

[73] Assignee: The University of Iowa Research Foundation, Iowa City, Iowa

[*] Notice: This patent is subject to a terminal disclaimer.

[21] Appl. No.: 08/812,979

[22] Filed: Mar. 5, 1997

Related U.S. Application Data

[62] Division of application No. 08/216,971, Mar. 23, 1994, Pat. No. 5,639,661.

[51] Int. Cl.[6] .......................... A01N 43/04; C07H 21/02; C12N 15/00; C12N 15/11
[52] U.S. Cl. .................. 514/44; 435/320.1; 536/23.1
[58] Field of Search ................... 514/44, 557, 21; 435/320.1, 375, 240.1, 252, 6, 325; 424/93.21; 5326/23.1, 23.5

[56] References Cited

U.S. PATENT DOCUMENTS 5,240,846  8/1993  Collins et al. ..................... 435/240.1

FOREIGN PATENT DOCUMENTS

| 0446017 A1 | 3/1991 | European Pat. Off. |
| WO9102796 | 3/1991 | WIPO |
| 2037478 | 4/1991 | WIPO |
| WO9110734 | 7/1991 | WIPO |

OTHER PUBLICATIONS

Marshall, E. (1995) Science 269:1050–1055.
Miller et al I (1995) FASEB J. 9:190–199.
Crystal, RG. (1995) Science 270:404–410.
Crystal R.G. Science. vol. 404–410, 1995.
Kolata G. New York Times. C3, Tuesday, Jul. 25, 1995.
Marshall E. vol. 269, 1050–1055, 1995.
Report and Recommendations of the panel to assess the NIH investment in research on Gene therapy. Dec. 7, 1995.
Fuller, et al., American Journal of Physiology, vol. 263, pp. C267–C286, Aug. 1992.
Kartner, et al., Nature Genetics, vol. 1, pp. 321–327 Aug. 1992.
Welsh, et al., Neuron, vol. 8, pp. 821–829, May 1992.
Yoshimura, et al., Nucleic Acids Research, vol. 20, No. 12, pp. 3233–3240, Apr. 7, 1992.
Bear, et al., Cell, vol. 68, pp. 809–818, Feb. 21, 1992.
Rosenfeld, et al., Cell, vol. 68, pp. 143–155, Jan. 10, 1992.
Smith, Alan E., Annual Reports in Medicinal Chemistry–27, Chapter 25, pp. 235–243, 1992.
Gregory, et al., Molecular and Cellular Biology, vol. 11, No. 8, pp. 3886–3893, Aug. 1991.
Rich, et al., Science vol. 253, pp. 205–207, Jul. 12, 1991.
Dörk, et al., Human Genetics, vol. 87, pp. 441–446, 1991.
Kerem, et al., Proc. Natl. Acad. Sci. USA, vol. 87, pp. 8447–8451, Nov. 1990.
Gregory, et al., Nature, vol. 347, pp. 382–386, Sep. 27, 1990.
Rich, et al., Nature, vol. 347, pp. 358–363, Sep. 27, 1990.
Drum, et al., Cell, vol. 62, pp. 1227–1233, Sep. 21, 1990.
Riordan, et al., Science, vol. 245, pp. 1066–1072, Sep. 8, 1989.

*Primary Examiner*—Brian R. Stanton
*Assistant Examiner*—Ram R. Shukla
*Attorney, Agent, or Firm*—Baker & Botts

[57] ABSTRACT

Disclosed are genes encoding novel CF monomer proteins which have cystic fibrosis transmembrane conductance regulator (CFTR) protein function.

5 Claims, No Drawings

GENES AND PROTEINS FOR TREATING CYSTIC FIBROSIS

This is a divisional application Ser. No. 08/216,971 filed on Mar. 23, 1994, now U.S. Pat. No. 5,639,661.

BACKGROUND OF THE INVENTION

Cystic Fibrosis (CF) is the most common fatal genetic disease in humans (Boat, T. F. et al. in The Metabolic Basis of Inherited Diseases (Scriver, C. R. et al. eds., McGraw-Hill, New York (1989))). Approximately one in every 2,500 infants in the United States is born with the disease. At the present time, there are approximately 30,000 CF patients in the United States. Despite current standard therapy, the median age of survival is only 26 years. Disease of the pulmonary airways is the major cause of morbidity and is responsible for 95% of the mortality. The first manifestation of lung disease is often a cough, followed by progressive dyspnea. Tenacious sputum becomes purulent due to colonization of bacteria. Chronic bronchitis and bronchiectasis can be partially treated with the current therapy, but the course is punctuated by increasingly frequent exacerbations of the pulmonary disease. As the disease progresses, the patient's activity is progressively limited. End-stage lung disease is heralded by increasing hypoxemia, pulmonary hypertension, and cor pulmonale.

The upper airways of the nose and sinuses are also involved by CF. Most patients develop chronic sinusitis. Nasal polyps occur in 15–20% of patients and are common by the second decade of life. Gastrointestinal problems are also frequent in CF; infants may suffer meconium ileus. Exocrine pancreatic insufficiency, which produces symptoms of malabsorption, is present in the large majority of patients with CF. Males are almost uniformly infertile and fertility is decreased in females.

Based on both genetic and molecular analyses, a gene associated with CF was isolated as part of 21 individual cDNA clones and its protein product predicted (Kerem, B. S. et al. (1989) Science 245:1073–1080; Riordan, J. R. et al. (1989) Science 245:1066–1073; Rommens, J. M. et al. (1989) Science 245:1059–1065)). European patent application publication number: 0 446 017 A1 describes the construction of the gene into a continuous strand, expression of the gene as a functional protein and confimation that mutations of the gene are responsible for CF. (See also Gregory, R. J. et al. (1990) Nature 347:382–386; Rich, D. P. et al. (1990) Nature 347:358–362).

The protein product of the CF associated gene is called the cystic fibrosis transmembrane conductance regulator (CFTR) (Riordan, J. R. et al. (1989) Science 245:1066–1073). CFTR is a protein of approximately 1480 amino acids made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) or P-glycoprotein, bovine adenyl cyclase, the yeast STE6 protein as well as several bacterial amino acid transport proteins (Riordan, J. R. et al. (1989) Science 245:1066–1073; Hyde. S. C. et al. (1990) Nature 346:362–365). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan, J. R. et al. (1989) Science 245:1066–1073; Frizzell, R. A. et al. (1986) Science 233:558–560; Welsh, M. J. and Liedtke, C. M. (1986) Nature 322:467; Li, M. et al. (1988) Nature 331:358–360; Hwang, T-C. et al. (1989) Science 244:1351–1353).

Sequence analysis of the CFTR gene of CF chromosomes has revealed a variety of disease causing mutations (Cutting, G. R. et al. (1990) Nature 346:366–369; Dean, M. et al. (1990) Cell 61:863:870; and Kerem, B-S. et al. (1989) Science 245:1073–1080; Kerem, B-S et al. (1990) Proc. Natl. Acad. Sci. USA 87:8447–8451). Population studies have indicated that the most common CF mutation, a deletion of the 3 nucleotides that encode phenylalanine at position 508 of the CFTR amino acid sequence (ΔF508), is associated with approximately 70% of the cases of cystic fibrosis. This mutation results in the failure of an epithelial cell chloride channel to respond to cAMP (Frizzell R. A. et al. (1986) Science 233:558–560; Welsh, M. J. (1986) Science 232:1648–1650.; Li, M. et al. (1988) Nature 331:358–360; Quinton, P. M. (1989) Clin. Chem. 35:726–730). In airway cells, this leads to an imbalance in ion and fluid transport. It is widely believed that this causes abnormal mucus secretion, and ultimately results in pulmonary infection and epithelial cell damage.

Studies on the biosynthesis (Cheng, S. H. et al. (1990) Cell 63: 827–834; Gregory, R. J. et al. (1991) Mol. Cell Biol. 11:3886–3893) and localization (Denning, G. M. et al. (1992) J. Cell Biol. 118:551–559) of CFTR ΔF508, as well as other CFTR mutants, indicate that many CFTR mutant proteins are not processed correctly and, as a result, are not delivered to the plasma membrane (Gregory, R. J. et al. (1991) Mol. Cell Biol. 11:3886–3893). These conclusions are consistent with earlier functional studies which failed to detect cAMP-stimulated chloride channels in cells expressing CFTR ΔF508 (Rich, D. P. et al. (1990) Nature 347:358–363; Anderson, M. P. et al. (1991) Science 251:679–682).

To date, the primary objectives of treatment for CF have been to control infection, promote mucus clearance, and improve nutrition (Boat, T. F. et al. in The Metabolic Basis of Inherited Diseases (Scriver, C. R. et al. eds., McGraw-Hill, New York (1989)). Intensive antibiotic use and a program of postural drainage with chest percussion are the mainstays of therapy. However, as the disease progresses, frequent hospitalizations are required. Nutritional regimens include pancreatic enzymes and fat-soluble vitamins. Bronchodilators are used at times. Corticosteroids have been used to reduce inflammation, but they may produce significant adverse effects and their benefits are not certain. In extreme cases, lung transplantation is sometimes attempted (Marshall, S. et al. (1990) Chest 98:1488).

Most efforts to develop new therapies for CF have focused on the pulmonary complications. Because CF mucus consists of a high concentration of DNA, derived from lysed neutrophils, one approach has been to develop recombinant human DNase (Shak, S. et al. (1990) Proc. Natl. Sci. Acad USA 87:9188). Preliminary reports suggest that aerosolized enzyme may be effective in reducing the viscosity of mucus. This could be helpful in clearing the airways of obstruction and perhaps in reducing infections. In an attempt to limit damage caused by an excess of neutrophil derived elastase, protease inhibitors have been tested. For example, alpha-1-antitrypsin purified from human plasma has been aerosolized to deliver enzyme activity to lungs of CF patients (McElvaney, N. et al. (1991) The Lancet 337:392). Another approach would be the use of agents to inhibit the action of oxidants derived from neutrophils. Although biochemical parameters have been successfully measured, the long term beneficial effects of these treatments have not been established.

Based on knowledge of the cystic fibrosis gene, three general corrective approaches (as opposed to therapies aimed at ameliorating the symptoms) are currently being pursued to reverse the abnormally decreased chloride secretion and increased sodium absorption in CF airways. Defective electrolyte transport by airway epithelia is thought to alter the composition of the respiratory secretions and mucus (Boat, T. F. et al. in The Metabolic Basis of Inherited Diseases (Scriver, C. R. et al. eds.), McGraw-Hill, New York (1989); Quinton, P. M. (1990) *FASEB J.* 4:2709–2717). Hence, pharmacological treatments aimed at correcting the abnormalities in electrolyte transport are being pursued. Trials are in progress with aerosolized versions of the drug amiloride; a diuretic that inhibits sodium channels, thereby inhibiting sodium absorption. Initial results indicate that the drug is safe and suggest a slight change in the rate of disease progression, as measured by lung function tests (Knowles, M. et al. (1990) *N. Eng. J. Med.* 322:1189–1194; App, E. (1990) *Am. Rev. Respir. Dis.* 141–605. Nucleotides, such as ATP or UTP, stimulate purinergic receptors in the airway epithelium. As a result, they open a class of chloride channel that is different from CFTR chloride channels. In vitro studies indicate that ATP and UTP can stimulate chloride secretion (Knowles, M. et al. (1991) *N. Eng. J. Med.* 325–533). Preliminary trials to test the ability of nucleotides to stimulate secretion in vivo, and thereby correct the electrolyte transport abnormalities are underway.

As with all pharmacological agents, issues such as drug toxicity and dosing will be important in developing an appropriate pharmacological agent for treating CF. A more fundamental consideration with pharmacological approaches to CF therapy is whether the chloride channel activity associated with CFTR is the crucial property that leads to the disease state. Perhaps there is another as yet, unidentified component of the CFTR system and this is the key regulator. If this were the case, it is possible that a pharmacological approach based on chloride transport might successfully adjust ion balance, but still not relieve the fundamental physiological problem.

A second approach to curing cystic fibrosis, "protein replacement" seeks to deliver functional, recombinant CFTR to CF mutant cells to directly augment the missing CFTR activity. The concept of protein replacement therapy for CF is simple: a preparation of highly purified recombinant CFTR formulated in some fusogenic liposome or reassembled virus carrier delivered to the airways by instillation or aerosol. However, attempts at formulating a CF protein replacement therapeutic have met with difficulties. For example, CFTR is not a soluble protein of the type that has been used for previous protein replacement therapies or for other therapeutic uses. There may be a limit to the amount of a membrane protein with biochemical activity that can be expressed in a recombinant cell. There are reports in the literature of $10^5$–$10^6$ molecules/cell representing the upper limit (H-Y Wang et. al *J. Biol. Chem* 264:14424 (1989)), compared to 2000 molecules/second/cell being reported for secreted proteins such as EPO, insulin, growth hormone, and tPA.

In addition to limited expression capabilities, the purification of CFTR, a membrane bound protein, is more difficult than purification of a soluble protein. Membrane proteins require solubilization in detergents. However, purification of CFTR in the presence of detergents represent a less efficient process than the purification process required of soluble proteins. Other potential obstacles to a protein replacement approach include: 1) the inaccessibility of airway epithelium caused by mucus build-up and the hostile nature of the environment in CF airways; 2) potential immrunogenicity; and 3) the fusion of CFTR with recipient cells may be an inefficient.

A third approach to cystic fibrosis treatment is a gene therapy approach in which DNA encoding cystic fibrosis is transferred to CF defective cells (e.g. of the respiratory tract). However, methods to introduce DNA into cells are generally inefficient. Since viruses have evolved very efficient means to introduce their nucleic acid into cells, many approaches to gene therapy make use of engineered defective viruses. However, viral vectors have limited space for accommodating foreign genes. For example, adeno-associated virus (AAV) although an attractive gene therapy vector in many respects, has only 4.5 Kb available for exogenous DNA. DNA encoding the full length CFTR gene represents the upper limit. Gene therapy approaches to CF will face many of the same clinical challenges as protein therapy.

Although there has been notable progress in developing curative therapies for CF based on knowledge of the gene encoding CFTR, the expressed protein product and mechanism of action, there are obstacles confronting every approach. New therapies for CF are needed.

SUMMARY OF THE INVENTION

The instant invention offers new therapies for treating Cystic Fibrosis, that are based on novel genes and proteins. In one aspect, the instant invention features genes encoding CF protein monomers, which have cystic fibrosis transmembrane conductance regulator activity. In a preferred embodiment, the gene encodes a CF protein monomer that consists essentially of a chloride ion channel and a regulator of the opening and closing of the chloride channel. In an especially preferred embodiment, the gene encodes a CF protein monomer consisting essentially of the membrane spanning domain-1 (MSD-1), the nucleotide binding domain-1 (NBD-1) and the R domain of naturally occurring CFTR. Further aspects of the invention include methods for making the disclosed genes, as well as preferred constructs and delivery vehicles encoding the genes for use in performing CF gene therapies.

In another aspect, the invention relates to CF protein monomers having cystic fibrosis transmembrane conductance regulator activity. In a preferred embodiment, the CF protein monomers consist essentially of a chloride ion channel, and a regulator of the opening and closing of the channel. In an especially preferred embodiment, the CF protein monomer consists essentially of the membrane spanning domain (MSD-1), the nucleotide binding domain-1 (NBD-1) and the R domain of naturally occurring CFTR. Further aspects of the instant invention include methods for making the disclosed protein, as well as preferred delivery vehicles for performing CF protein replacement therapies.

The gene sequences encoding CF protein monomers as disclosed herein are at least 40% shorter than the sequence encoding full length CFTR (about 4.3 kb) and therefore are better accommodated by available gene therapy vectors. In addition, the shorter sequence CF protein monomer gene can be more easily expressed than full-length CFTR. Further, the expressed CF protein monomers are more soluble and therefore are more readily purified from host cells than full length CFTR. These advantages and more make the CF protein monomer genes and proteins attractive as gene therapy and protein replacement therapeutics for Cystic Fibrosis patients.

DETAILED DESCRIPTION OF THE INVENTION

The instant invention is based on the surprising finding (described in greater detail in Example 1) that a defective gene construct, namely a construct encoding only NBD-1, MSD-1 and the R domain of the CFTR dimer, expresses a protein having normal CFTR activity. Based on this finding, the invention features methods for making genes that express CF protein monomers having CFTR activity. The CF genes and protein monomers can be used for example therapeutically in CF gene and protein replacement therapies.

As used herein, the following words and phrases have the meaning set forth below:

"gene" shall mean a sequence of genetic material (e.g. DNA and RNA) that carries the information representing a protein.

Unless otherwise indicated, "protein" shall mean a protein, polypeptide or peptide.

"CFTR or Cystic Fibrosis Transmembrane Conductance Regulator protein"—refers to a 1480 amino acid protein containing two membrane-spanning domains (MSDs), two nucleotide binding domains (NBDs) and a unique R domain, that functions as a chloride channel regulated by phosphorylation and by nucleoside triphosphates.

The phrase "cystic fibrosis transmembrane conductance regulator (CFTR) activity or function"—is meant to refer to functions normally performed by wild-type CFTR. Such functions can include mediation of ion, (e.g. chloride ion) transport across cellular membranes.

A "Cystic Fibrosis (CF) defective cell" is a cell that lacks cystic fibrosis transmembrane conductance regulator function. Examples include CF mutants of which over 200 different varieties have been identified to date (see for example Tsui, L-C (1992) "The Spectrum of Cystic Fibrosis Mutations" *Trends in Genetics* 8 (11) 329–398).

"CF protein monomer" shall mean a monomeric protein, polypeptide or peptide portion of CFTR that is capable of functioning as a chloride channel pore. For example, as shown herein, a CF protein monomer exhibiting CFTR activity can comprise the R domain, NBD-1 and MSD-1 of natural CFTR.

"R (regulator) domain" refers to a domain that keeps a chloride channel closed at rest and which opens the channel when phosphorylated (e.g. by cAMP-dependent protein kinase (PKA) or protein kinase C (PKC)). The R domain of CFTR is encoded by exon 13, and generally comprises 241 amino acid residues that span from about amino acid residues 590 to 830 of full length CFTR or a lesser portion within this stretch.

"NBD or Nucleotide Binding Domain" refers to a domain that binds nucleotides (e.g. adenosine triphosphate (ATP)). NBD-1 or Nucleotide Binding Domain-1 refers to the amino terminal nucleotide binding domain of CFTR generally comprising a sequence that spans from about amino acid residues 360 to 708 or a lesser portion within this stretch.

"MSD or Membrane Spanning Domain" refers to a domain that forms a chloride channel. MSD-1 or Membrane Spanning Domain-1" refers to the amino terminal membrane spanning domain that spans from about amino acid residues 76 to 360 or a lesser portion within this stretch.

"CF gene therapy" refers to the transfer of genetic material (e.g., DNA or RNA) encoding CFTR functional activity into a host to treat or prevent Cystic Fibrosis (CF).

"CF protein replacement therapy" refers to transfer of a protein having CFTR functional activity into a host to treat or prevent CF.

Methods for obtaining genes encoding CF protein monomers

The nucleotide and amino acid sequence for full-length CFTR and modifications encoding CF mutants are known in the art (See for example, European patent application publication number: 0 446 017 A1). Based on this information, one of skill in the art can obtain genes encoding CF protein monomers using techniques that are well-known. For example, genes encoding CFTR can be isolated from appropriate cells or plasmids using standard techniques (e.g. restriction enzyme cleavage). Genetic material encoding full-length CFTR can then be modified (e.g. via site-directed mutagenesis) to obtain a gene encoding a CF protein monomer. Alternatively, a CF protein monomer gene can be generated synthetically using standard modes of polynucleotide synthesis. A candidate gene can be tested to determine whether it in fact encodes functional CFTR activity for example using the SPQ assay disclosed in detail in the following Example 2.

An "expression cassette" comprising the gene encoding a CF protein monomer operably linked or under the control of transcriptional and translational regulatory elements (e.g. a promoter, ribosome binding site, operator, or enhancer) can be made and used for expression of CF protein monomers in vitro or in vivo. The choice of regulatory elements employed may vary, depending for example on the host cell to be transfected and the desired level of expression. Several promoters for use in mammalian cells are known in the art and include, for example, the phosphoglycerate (PGK) promoter, the simian virus 40 (SV 40) early promoter, the Rous sarcoma virus (RSV) promoter, the adenovirus major late promoter (MLP) and the human cytomegalovirus (CMV) immediate early 1 promoter. However, any promoter that facilitates suitable expression levels can be used in the instant invention. Inducible promoters, (e.g. those obtained from the heat shock gene, metallothionein gene, beta interferon gene, or steroid hormone responsive genes) may be useful for regulating transcription based on external stimuli.

A particularly preferred gene encoding a CF protein monomer comprising the membrane-spanning domain (MSD)-1, nucleotide binding domain (NBD)-1 and the R domain of natural CFTR consists of nucleotides 1–2638 of full length CFTR. This gene (SEQ ID NO. 1) encodes an 836 amino acid fragment of fill length CFTR protein (SEQ ID NO 2). Methods for producing this gene and protein are described in detail in Example 1. The gene may be further modified, for example, to increase stability, by the addition of a carboxy terminal moiety from CFTR or another membrane protein.

Methods for making CF protein monomers

Genes encoding CF protein monomers (preferably in a suitable expression cassette), can be introduced into cells in culture using standard techniques (e.g. via calcium phosphate or calcium chloride co-precipitation, DEAE dextran mediated transfection, lipofection, or electroporation). Recombinant cells can then be cultured in vitro in a manner that allows expression of CF protein monomers. Preferred host cells for generating CF protein monomers include for example; mammalian cells, such as COS and C127; yeast cells and insect cells.

CF protein monomers are integral membrane proteins that can be purified from host cell membranes using known methods, such as ion exchange chromatography, gel filtration chromatography, electrophoresis and affinity chromatography. (Tilly et. al. (1992) *The Journal of Biological Chemistry*, Vol 267, No. 14, pp. 9470–73; Anderson et. al. (1991) *Science* 251, pp. 679–682). A preferred method of purification involves first solubilizing the protein in the presence of a nondenaturing detergent.

As an alternative to recombinant methods, CF protein monomers can also be obtained from CFTR protein, by enzymatic cleavage, for example.

CF protein monomers produced as described herein can be used, for example, as an immunogen to generate antibodies specific to the amino terminal portion of CFTR. In addition, the protein monomer can be used in research to determine the function of a particular region or domain of CFTR. The protein monomer can also be used in protein replacement therapies and the gene in gene therapies for Cystic Fibrosis as described in detail below.

Protein Replacement Therapy

Protein therapy may be accomplished by any method that effectively introduces CF protein monomers into the membrane of CF defective cells to imbue on those cells CFTR activity. An effective amount of a CF protein monomer (i.e. an amount sufficient to reduce or eliminate the symptoms associated with CF) can be administered alone or in association with an agent that facilitates passage (e.g. via fusion or endocytosis) through cell membranes to CF patients (i.e. patients having CF defective cells). The "effective amount" can be determined by one of skill in the art based on such factors as the type and severity of symptoms being treated, the weight and/or age of the subject, the previous medical history of the subject, and the selected route for administration of the agent.

Preferably for use in protein therapy, CF protein monomers are associated with lipids, such as detergents or other amphipathic molecule micelles, membrane vesicles, liposomes, virosomes, or microsomes. Lipid compositions that are naturally fusogenic or can be engineered to become fusogenic (e.g. by incorporating a fusion protein into the lipid) are especially preferred. Fusion proteins can be obtained from viruses such as parainfluenza viruses 1–3, respiratory syncytial virus (RSV), influenza A, Sendai virus, and togavirus fusion protein. Nonviral fusion proteins include normal cellular proteins that mediate cell-cell fusion. Other nonviral fusion proteins include the sperm protein PH-30 which is an integral membrane protein located on the surface of sperm cells that is believed to mediate fusion between the sperm and the egg. See Blobel et al. (1992) *Nature* 356:248–251. Still other nonviral fusion proteins include chimaeric PH-30 proteins such as PH-30 and the binding component of hemaglutinin from influenza virus and PH-30 and a disintegrin (e.g. bitistatin, barbourin, kistrin, and echistatin). In addition, lipid membranes can be fused using traditional chemical fusogens such as polyethylene glycol (PEG).

A CF patient can be treated by administration of an effective amount of a CF protein monomer, optionally in a pharmaceutically acceptable carrier or diluent. An effective amount of a CF protein monomer is an amount sufficient alleviate the symptoms of CF. A CF protein monomer can be administered subcutaneously, intravenously, intraperitoneally, intramuscularly, parenterally, orally, submucosally, by inhalation, or other appropriate route of administration in an effective dosage range. A preferred route of administration is by inhalation (e.g. of an aerosolized pharmaceutical composition). If necessitated by a particular mode of administration, CF protein monomers can be encapsulated within a material that protects it from enzymatic degradation. In addition, prior to administration, it may be useful to administer agents to clear mucus (e.g. using a DNAse) and/or bacterial infection.

Gene Therapy

Alternatively, a preparation of the gene encoding a CF protein monomer can be incorporated into a suitable vector for delivering the gene into a CF patient's defective cells. As many of the symptoms of CF manifest themselves in the respiratory tract, the preparation can be delivered directly to the airways of CF patients.

The first generation of CF gene therapy is likely to be transient and to require repeated delivery to the airways. Eventually, however, gene therapy may offer a cure for CF when the identity of the precursor or stem cell to air epithelial cells becomes known. If genetic material encoding CF protein monomers were incorporated into airway stem cells, all subsequent generations of such cells would make authentic CF monomer from the integrated sequences and would correct the physiological defect almost irrespective of the biochemical basis of the action of CFTR.

For use in treating CF, appropriate vectors must: 1) effectively infect lung epithelia or other tissue manifesting the disease and deliver the therapeutic nucleic acid encoding CFTR function; 2) be appropriately maintained in host cells; and 3) be safe. The following describes a number of approaches and vectors that may prove useful for performing CF gene therapy. The following listing, however, is not intended to be exhaustive and many other vectors should prove useful for performing gene therapy with the novel genes disclosed herein.

Retroviruses—Although defective retroviruses are the best characterized system and so far the only one approved for use in human gene therapy (Miller, A. D. (1990) *Blood* 76:271), the major issue in relation to CF is the requirement for dividing cells to achieve DNA integration and gene expression. Were conditions found to induce airway cell division, the in vivo application of retroviruses, especially if repeated over many years, would necessitate assessment of the safety aspects of insertional mutagenesis in this context.

Adeno-Associated Virus—(AAV) is a naturally occurring defective virus that requires other viruses such as adenoviruses or herpes viruses as helper viruses(Muzyczka, N.(1992) in *Current Topics in Microbiology and Immunology* 158:97). It is also one of the few viruses that may integrate its DNA into non-dividing cells, although this is not yet certain. Vectors containing as little as 300 base pairs of AAV can be packaged and can integrate, but space for exogenous DNA is limited to about 4.5 kb. AAV vectors therefore may prove useful for expressing genes encoding CF protein monomers, although genes encoding fall length CFTR approach AAV's upper limit.

Naked DNA—Naked plasmid can be introduced into muscle cells by injection into the tissue. Expression can extend over many months but the number of positive cells is low (Wolff, J. et al. (1989) *Science* 247:1465).

DNA-Lipid Complexes—Lipid carriers can be associated with naked DNA (e.g. plasmid DNA) to facilitate passage through cellular membranes. Cationic, anionic, or neutral lipids can be used for this purpose. However, cationic lipids are preferred because they associate better with DNA, which generally has a net negative charge. Cationic lipids have been shown to mediate intracellular delivery of plasmid DNA (Felgner, P. and Ringold, G. M. (1989) *Nature* 337:387). Injection of cationic lipid plasmid DNA complexes into the circulation of mice has been shown to result in expression of the DNA in lung (Brigham, K. et al. (1989) *Am. J. Med. Sci.* 298:278). Instillation of cationic lipid plasmid DNA into lung has also been found to be expressed in epithelial cells but the efficiency of expression has been reported as being relatively low and transient (Hazinski, T. A. et al. (1991) *Am. J Respir., Cell Mol. Biol.* 4:206).

Receptor Mediated Entry—In an effort to improve the efficiency of plasmid DNA uptake, attempts have been made to utilize receptor-mediated endocytosis as an entry mechanisms and to protect DNA in complexes with polylysine (Wu, G. and Wu, C. H. (1988) *J. Biol. Chem.* 263:14621). One potential problem with this approach is that the incoming plasmid DNA enters the pathway leading from endosome to lysosome, where much incoming material is degraded. One solution to this problem is the use of transferrin DNA-polylysine complexes linked to adenovirus capsids (Curiel, D. T. et al. (1991) *Proc. Natl. Acad. Sc. USA* 88:8850). The latter enter efficiently but have the added advantage of naturally disrupting the endosome thereby avoiding shuttling to the lysosome Adenovirus—Defective adenoviruses at present appear to be a promising approach to CF gene therapy (Berkner, K. L. (1988) *BioTechniques* 6:616). Adenovirus can be manipulated such that it encodes and expresses the desired gene product, and at the same time is inactivated in terms of its ability to replicate in a normal lytic viral life cycle. In addition, adenovirus has a natural tropism for airway epithelia. The viruses are able to infect quiescent cells as are found in the airways, offering a major advantage over retroviruses. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109:233–238). Finally, adenovirus mediated gene transfer has been demonstrated in a number of instances including transfer of alpha-1-antitrypsin and CFTR to the lungs of cotton rats (Rosenfeld, M. A. et al. (1991) *Science* 252:431–434; Rosenfeld et al., (1992) *Cell* 68:143–155). Furthermore, extensive studies to attempt to establish adenovirus as a causative agent in human cancer were uniformly negative (Green, M. et al. (1979) *Proc. Natl. Acad. Sci. USA* 76:6606).

The following properties would be desirable in the design of an adenoviris vector to transfer the gene for a CF protein monomer to the airway cells of a CF patient. The vector should allow sufficient expression of the CF protein monomer, while producing minimal viral gene expression. There should be minimal viral DNA replication and ideally no virus replication. Finally, recombination to produce new viral sequences and complementation to allow growth of the defective virus in the patient should be minimized.

A first generation adenovirus encoding full length CFTR has been prepared and includes viral DNA derived from the common relatively benign adenovirus 2 serotype. A similar vector can be prepared to express CF protein monomer. The E1a and E1b regions of the viral genome, which are involved in early stages of viral replication have been deleted. Their removal impairs viral gene expression and viral replication. The protein products of these genes also have immortalizing and transforming function in some non-permissive cells.

The CF protein monomer coding sequence can be inserted into the viral genome in place of the E1a/E1b region and transcription of the CF protein monomer sequence will be driven by the endogenous E1a promoter. This is a moderately strong promoter that is functional in a variety of cells. In contrast to some adenovirus vectors (Rosenfeld, M. et al. (1992) *Cell* 68:143), this adenovirus retains the E3 viral coding region. As a consequence of the inclusion of E3, the length of the adenovirus-CFTR DNA is greater than that of the wild-type adenovirus. The greater length of the recombinant viral DNA renders it more difficult to package. This means that the growth of the Ad2/CFTR virus is impaired even in permissive cells that provide the missing E1a and E1b functions.

The E3 region of the Ad2 vector encodes a variety of proteins. One of these proteins, gp19, is believed to interact with and prevent presentation of class 1 proteins of the major histocompatability complex (MHC) (Gooding, C. R. and Wold, W. S. M. (1990) *Crit. Rev. Immunol.* 10:53). This property prevents recognition of the infected cells and thus may allow viral latency. The presence of E3 sequences, therefore, has two useful attributes; first, the large size of the viral DNA renders it doubly defective for replication (i.e., it lacks early functions and is packaged poorly) and second, the absence of MHC presentation could be useful in later applications of Ad2/CFTR-1 in gene therapy involving multiple administrations because it may avoid an immune response to recombinant virus containing cells.

Not only are there advantages associated with the presence of E3; there may be disadvantages associated with its absence. Studies of E3 deleted virus in animals have suggested that they result in a more severe pathology (Gingsberg, H. S. et al. (1989) *Proc. Natl. Acad. Sci (USA)* 86:3823). Furthermore, E3 deleted virus, such as might be obtained by recombination of an E1 plus E3 deleted virus with wild-type virus, is reported to outgrow wild-type in tissue culture (Barkner, K. L. and Sharp, P. (1983) *Nucleic Acids Research* 11:6003). By contrast, however, a recent report of an E3 replacement vector encoding hepatitis B surface antigen, suggests that when delivered as a live enteric vaccine, such a virus replicates poorly in human compared to wild-type.

The adenovirus vector Ad2 vector can be grown in human 293 cells. These cells contain the E1 region of adenovirus and constitutively express E1a and E1b, which complement the defective adenoviruses by providing the products of the genes deleted from the vector.

In addition to Ad2, other varieties of adenovirus (e.g., Ad3, Ad5, and Ad7) may also prove usefull as gene therapy vectors. This may prove essential if immune response against a single serotype reduces the effectiveness of the therapy.

Adenoviral vectors currently in use retain most ($\geq 80\%$) of the parental viral genetic material leaving their safety untested and in doubt. Second-generation vector systems containing minimal adenoviral regulatory, packaging and replication sequences have therefore been developed.

An adenoviral construct expressing only the open reading frame 6 (ORF6) of adenoviral early region 4 (E4) from the E4 promoter and which is deleted for all other known E4 open reading frames was constructed. Expression of E4 open reading frame 3 is also sufficient to provide E4 functions required for DNA replication and late protein synthesis. However, it provides these functions with reduced efficiency compared to expression of ORF6, which will likely result in lower levels of virus production. Therefore expressing ORF6, rather than ORF3, appears to be a better choice for producing recombinant adenovirus vectors.

The E4 region of adenovirus is suspected to have a role in viral DNA replication, late mRNA synthesis and host protein synthesis shut off, as well as in viral assembly (Falgout, B. and G. Ketner (1987) *J. Virol.* 61:3759–3768). Adenovirus early region 4 is required for efficient virus particle assembly. Adenovirus early region 4 encodes functions required for efficient DNA replication, late gene expression, and host cell shutoff. Halbert, D. N. et al. (1985) *J. Virol.* 56:250–257.

The deletion of non-essential open reading frames of E4 increases the cloning capacity of recombinant adenovirus vectors by approximately 2 kb of insert DNA without significantly reducing the viability of the virus in cell culture. When placed in combination with deletions in the E1 and/or E3 regions of adenovirus vectors, the theoretical insert capacity of the resultant vectors is increased to 8–9 kb. An example of where this increased cloning capacity may prove usefull is in the development of a gene therapy vector encoding CFTR. As described above, the first generation adenoviral vector approaches the maximum packaging capacity for viral DNA encapsidation. As a result, this virus grows poorly and may occasionally give rise to defective progeny. Including an E4 deletion in the adenovirus vector should alleviate these problems. In addition, it allows flexibility in the choice of promoters to drive CFTR expression from the virus. For example, strong promoters such as the adenovirus major late promoter, the cytomegalovirus immediate early promoter or a cellular promoter such as the CFTR promoter, which may be too large for first-generation adenovirus can be used to drive expression.

In addition, by expressing only ORF6 of E4, these second generation adenoviral vectors may be safer for use in gene therapy. Although ORF6 expression is sufficient for viral DNA replication and late protein synthesis in immortalized cells, it has been suggested that ORF6/7 of E4 may also be required in non-dividing primary cells (Hemstrom, C. et al. (1991) *J. Virol.* 65:1440–1449). The 19 kD protein produced from open reading frame 6 and 7 (ORF6/7) complexes with and activates cellular transcription factor E2F, which is required for maximal activation of early region 2. Early region 2 encodes proteins required for viral DNA replication. Activated transcription factor E2F is present in proliferating cells and is involved in the expression of genes required for cell proliferation (e.g., DHFR, c-myc), whereas activated E2F is present in lower levels in non-proliferating cells. Therefore, the expression of only ORF6 of E4 should allow the virus to replicate normally in tissue culture cells (e.g., 293 cells), but the absence of ORF6/7 would prevent the potential activation of transcription factor E2F in non-dividing primary cells and thereby reduce the potential for viral DNA replication.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example 1

Expression of a CF Protein Monomer Generates Total CFTR Activity Materials and Methods D836X was constructed in the vaccinia virus expression plasmid pTM-CFTR4 (Cheng et al., Cell 63, 827–834 1990), as previously described (Kunkel, Proc Natl Acad Sci. U.S.A. 82, 488–492 1985; Gregory et al., Nature 347, 382–386 1990). For the amino terminal portion of CFTR amino acids 1–836 were used. This sequence includes MSD1, NBD1 and the R domain (defined as the boundaries of exon 13, residues 590 to 830). In D836X, X represents a stop codon replacing the aspartate at residue 836.

Wild-type and mutant CFTRs were transiently expressed in HeLa cells using the vaccinia virus/bacteriophage T7 hybrid expression system, as previously described (Elroy-Stein et al., Proc Natl Acad Sci U.S.A. 86, 6126–6130 1989; Anderson et al., Cell 67, 775–784 1991a). Cells (60–80% confluent, 8–24 h after seeding) were infected at a multiplicity of infection of 10–20. For protein expression studies, cell lysates were harvested 15 h after infection. For electrophysiology, cells were assayed for Cl⁻ channel function 15–30 h after infection.

Wild-type and mutant CFTR proteins were immunoprecipitated from digitonin-solubilized lysates of HeLa cells using monoclonal antibodies against the R domain (exon 13/β-galactosidase fusion protein; M13-1) and the carboxyl terminus (amino acids 1477–1480; M24-1) of CFTR (Gregory et al., Nature 347, 382–386 1990; Marshall et al., J Biol Chem In Press). The antibody-CFTR complex was labeled by phosphorylation with [g-$^{32}$P]ATP and the catalytic subunit of cAMP-dependent protein kinase (PKA), electrophoresed on 8% SDS-polyacrylamide gels and autoradiographed (Gregory et al., Nature 347, 382–386 1990; Cheng et al., Nature 347, 382–386 1990).

Whole-cell and single-channel currents were recorded, as previously described (Hamill et al., Pfluegers Arch 391, 85–100 1981; Sheppard et al., Nature 362, 160–164 1993). Experiments were conducted at 34–36 _C. The established sign convention was used throughout. Liquid junction potentials and potentials at the tip of the patch-pipette were measured and I-V relationships corrected for the corresponding offset.

For whole-cell experiments, the pipette (internal) solution contained (in mM): 120 N-methyl-D-glucamine (NMDG), 85 aspartic acid, 3 MgCl$_2$, 1 CsEGTA (ethyleneglycol-bis-(β-aminoethylether) N,N,N',N',-tetraacetic acid, cesium salt), 1 MgATP and 5 TES (N-Tris(hydroxymethyl)methyl-2-aminoethane sulfonic acid), pH 7.3 with HCl ([Cl⁻], 43 mM; $[Ca^{2+}]_{free} < 10^{-8}$ M). The bath (external) solution contained (in mM): 140 NaCl, 1.2 MgSO$_4$, 1.2 CaCl$_2$, 10 dextrose and 10 TES, pH 7.3 with NaOH ([Cl⁻], 142 mM). Whole-cell currents were filtered at 0.5 kHz and digitized at 2 kHz.

For experiments with excised inside-out membrane patches, the pipette (extracellular) solution contained (in mM): 140 NMDG, 140 aspartic acid, 5 CaCl$_2$, 2 MgSO$_4$ and 10 TES, pH 7.3 with Tris ([Cl⁻], 10 mM). The bath (intracellular) solution contained (in mM): 140 NMDG, 3 MgCl$_2$, 1 CsEGTA and 10 TES, pH 7.3 with HCl ([Cl⁻], 147 mM; $[Ca^{2+}]_{free} < 10^{-8}$ M). Single-channel currents were filtered at 1 kHz and digitized at 10 kHz. Single-channel current amplitudes were determined from the fit of Gaussian distributions to current amplitude histograms. The fit of linear least squares regression lines to single-channel I-V relationships was used to determine single-channel conductance at negative voltages, where the I-V relationship was linear (Sheppard et al., Nature 362, 160–164 1993). Single-channel open-state probability ($P_o$) was measured in patches containing _4 channels and in current recordings of at least 100 s duration. The number of channels in each patch was determined from the maximum number simultaneously open with 2.27 mM MgATP in the intracellular solution after PKA-dependent phosphorylation. Data were analyzed using pClamp software (Axon Instruments, Inc., Foster City, Calif.).

Triton X-100 solubilized lysates from unlabeled cells were centrifuged on 5 to 20% sucrose gradients (Gradient Master, BioComp Instruments Inc., Fredericton, Canada) in 0.5 M NaCl, 50 mM Tris-HCl, pH 7.4, 0.1 mM phenylmethylsulfonyl fluoride, and 0.75 mM benzamidine-HCl with 0.1% TX-100 for 2.5 h at 215, 000×g at 4_C. Gradients were fractionated from the top and fractions were immunoprecipitated with antibody to the R domain, phosphorylated and electrophoresed, as described above. The amount of immunoprecipitated and phosphorylated D836X or CFTR in each fraction was then quantitated by radioanalytic scanning (AMBIS Systems Inc., San Diego, Calif.).

Results are expressed as mean ±SEM of n observations. To compare mean values, we used Student's t-test. Differences were considered statistically significant when the p value was <0.05.

Results

D836X was transiently expressed in HeLa cells and its immunoreactivity compared with that of wild-type CFTR. Two antibodies: M13-1 against the R domain, which is present in D836X, and M24-1 against the carboxyl terminus, which is absent in D836X were used. M13-1, but not M24-1 immunoprecipitated a protein of about 85 kDa, consistent with the predicted size of D836X (about 92 kDa). As expected, both antibodies recognized wild-type CFTR. Because D836X lacks glycosylation sites, the processing of this mutant through the Golgi complex cannot be assessed by examining its migration on an SDS-polyacrylamide gel (Cheng et al., Cell 63, 827–834 1990).

To assess the function of D836X, the patch-clamp technique was used. Table 1 compares the properties of D836X whole-cell currents with those of wild-type CFTR. Under basal conditions, D836X whole-cell currents were small, but the amount of basal current appeared to be greater than that observed either in cells infected with control virus alone or in cells expressing wild-type CFTR. However, the difference was not statistically significant (p=0.23). Addition of cAMP agonists reversibly activated whole-cell current in cells expressing D836X, although the magnitude of the increase was much less than that observed in cells expressing wild-type CFTR. D836X whole-cell currents, like those of wild-type CFTR, showed no evidence of voltage-dependent activation or inactivation either before or after stimulation (not shown).

TABLE 1

Comparison of D836X and wild-type CFTR whole-cell currents.

|  | (n) | Current at +50 mV (pA/pF) Basal | Current at +50 mV (pA/pF) cAMP | Current at +50 mV (pA/pF) Wash | Cell Capacitance (pF) |
|---|---|---|---|---|---|
| D836X(10) | 4.5 ± 1.7 | 10.6 ± 3.0 | 2.7 ± 1.1 | 42.4 ± 3.5 | |
| CFTR(6) | 1.8 ± 0.2 | 99.0 ± 20.8 | 4.7 ± 0.9 | 35.6 ± 3.1 | |

| Anion-to-Cation Permeability ($P_{Na}/P_{Cl}$) | | |
|---|---|---|
| | Basal | cAMP |
| D836X(6) | 0.14 ± 0.03 | 0.17 ± 0.02 |
| CFTR(6) | 0.48 ± 0.10 | 0.03 ± 0.02 |

| Relative Anion Permeability ($P_X/P_{Cl}$) | | |
|---|---|---|
| | $Br^-$ | $Cl^-$ | $I^-$ |
| D836X(3–4) | 1.26 ± 0.03 | 1.0 | 0.65 ± 0.10 |
| CFTR(3–4) | 1.26 ± 0.06 | 1.0 | 0.66 ± 0.08 |

| Relative Anion Conductance ($G_X/G_{Cl}$) | | |
|---|---|---|
| | $Br^-$ | $Cl^-$ | $I^-$ |
| D836X(3–4) | 1.00 ± 0.19 | 1.0 | 0.33 ± 0.06 |
| CFTR(3–4) | 1.21 ± 0.12 | 1.0 | 0.17 ± 0.01 |

Data are mean ±SEM of values calculated from currents in individual cells (n, number of cells) under basal, cAMP (10 μM forskolin, 100 μM IBMX and 500 μM 8-(4-chlorophenylthio)-adenosine 3':5'-cyclic monophosphate sodium salt, CPT-cAMP) and wash conditions. Currents at +50 mV for cells infected with control virus alone were 1.3±0.3 pA/pF (basal) and 0.3±0.0 pA/pF (cAMP); cell capacitance was 31.6±5.7; n=6. Permeability and conductance ratios of anions (X-) were determined in the presence of cAMP agonists, as previously described (Anderson et al, 1991b). I-V relationships were obtained by a 400 ms ramp of voltage; holding voltage was −40 mV.

Under basal conditions, whole-cell currents from cells expressing D836X had a relatively linear current-voltage (I-V) relationship and a reversal potential consistent with $Cl^-$-selectivity, whereas basal whole-cell currents from cells expressing wild-type CFTR were much less $Cl^-$-selective (Table 1). However, after addition of cAMP agonists, whole-cell currents from both groups of cells were $Cl^-$-selective. The anion permeability and conductance sequences of D836X whole-cell currents were similar to those of wild-type CFTR ($Br^->Cl^->I^-$; Table 1).

Although many properties of the D836X whole-cell currents resembled those of wild-type CFTR, two differences were observed. First, the tendency for cells expressing D836X to have larger basal whole-cell currents, and more convincingly, the $Cl^-$-selectivity of basal currents suggested that D836X channels might have some activity even without cAMP stimulation (the pipette solution contained 1 mM MgATP). Second, the magnitude of cAMP-activated D836X whole-cell currents was reduced compared to that of wild-type CFTR (p<0.001).

These data suggest that the amino-terminal portion of CFTR forms a regulated $Cl^-$ channel. In contrast, the carboxyl-terminal portion of CFTR (R domain, MSD2 and NBD2, containing residues 1,2 and 708–1480) did not generate functional $Cl^-$ channels despite producing protein of the expected size and immunoreactivity (not shown).

To better understand the function of the amino-terminal portion of CFTR, the single-channel properties of D836X was compared with those of wild-type CFTR, using excised inside-out membrane patches. After excision of membrane patches from cells expressing D836X, no channel activity was observed. However, as soon as ATP was added to the cytosolic surface (0.88 mM MgATP), channels opened and the open-state probability ($P_o$) was approximately 0.1. This result contrasts sharply with the behavior of wild-type CFTR: in the presence of intracellular MgATP alone, the $P_o$ of wild-type CFTR $Cl^-$ channels was zero. Phosphorylation with PKA (75 nM) significantly increased the $P_o$ of D836X channels. As previously described, phosphorylation with PKA was required to open wild-type CFTR $Cl^-$ channels (Chang et al., 1993; Cheng et al., 1991; Rich et al., 1993). Once phosphorylated, D836X and CFTR channels had similar $P_o$ values. These data suggest that some aspects of the relationship between the R domain and the rest of the channel may be altered in D836X while others may remain intact.

The conductive properties of D836X appeared to be the same as those of wild-type CFTR. The single-channel current amplitude was found to be similar. However, the single-channel slope conductance of D836X (8.03±0.23 pS; n=6) was not different from that of wild-type CFTR (8.29±0.15 pS; n=4).

Whole-cell current (I) is determined by the number of channels in the plasma membrane (N), $P_o$, and single-channel current amplitude (i): $I = N \cdot i \cdot P_o$. The finding that D836X has i and $P_o$ values comparable to those of wild-type CFTR suggests that whole-cell current is reduced in cells expressing D836X because N, the number of functional $Cl^-$ channels in the plasma membrane, is decreased. Consistent with this interpretation is the finding that cAMP-activated whole-cell currents were observed in 10 of 59 cells expressing D836X (17%), compared with 10 of 14 cells expressing wild-type CFTR (71%). Thus, D936X was not as efficient as wild-type at generating functional channels.

Once phosphorylated with PKA, wild-type CFTR Cl⁻ channels require cytosolic MgATP to open. Previous studies have suggested that MgATP interacts with both NBD1 and NBD2 to regulate the channel (Anderson and Welsh, 1992; Smit et al., 1993). Because D836X lacks NBD2, the interaction with intracellular nucleotides might be altered. To test this hypothesis, the effect of intracellular MgATP on channels that had been phosphorylated with PKA was examined. As previously observed for wild-type CFTR, increasing concentrations of MgATP increased the activity of D836X. However, D836X Cl⁻ channels had higher $P_o$ values at MgATP concentrations between 0.09 and 0.88 mM than did wild-type CFTR Cl⁻ channels. This difference was particularly dramatic at the lowest MgATP concentrations tested. As was previously reported for wild-type CFTR (Anderson and Welsh, 1992), an Eadie-Hofstee plot of the D836X data generated a curved line. One possible interpretation of a curved line in such a plot is that there is kinetic cooperativity, perhaps with ATP interacting with more than one site in a functional channel.

Previous studies of wild-type CFTR showed that cytosolic ADP inhibited the channel (Anderson and Welsh, 1992). Based on studies of variants containing site-directed mutations in the two NBDs, it was suggested that ADP interacted with NBD2. Therefore, whether ADP would inhibit D836X Cl⁻ channels, which lack NBD2 was of interest. It was found that intracellular ADP (1 mM) produced equivalent reductions in the activity of both D836X and wild-type channels.

Based on these results and considerations discussed below, it was asked whether D836X might exist as a multimer. To test this possibility, its migration on sucrose density gradients was examined. It was found that in the presence of Triton X-100 (TX-100), D836X sediments in the middle of a 5–20% sucrose gradient. This corresponds to the sedimentation of the standard protein marker aldolase (158 kDa), which is double that expected for the predicted molecular weight of D836X and is similar to the migration of wild-type CFTR. D836X was found to also migrated in the same fractions as CFTR when sedimented in 10–30% TX-100 gradients or in 5–20 or 10–30% 3-[(3-Cholamidopropyl)dimethyl-ammonio]-1-propanesulfonate (CHAPS) gradients. These sedimentation patterns suggest that D836X associates to form a multimer of two or more subunits.

Example 2

Assessment of Functional Activity Using SPQ.

cAMP-dependent Cl⁻ channel activity was assessed using the halide-sensitive fluorophore 6-methoxy-N-(3-sulfopropyl)-quinolinium (SPQ) (Molecular Probes), as previously described (Illsley and Verkiman, (1987) Biochem 26:1215–1219). In this assay, an increase in halide permeability results in a more rapid increase in SPQ fluorescence. The rate of change rather than the absolute change in fluorescence is the important variable in assessing anion permeability. Differences between groups in absolute levels may reflect quantitative differences between groups in SPQ loading, size of cells or number of cells studied (Illsley and Verkman, 1987). Fluorescence of SPQ in single cells can be measured with a Nikon inverted microscope, a digital imaging system from Universal Imaging and a Hamamatsu ICCD camera.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. An isolated DNA molecule consisting of sequence of SEQ D NO: 1.

2. A vector comprising the isolated DNA molecule of claim 1.

3. The vector of claim 2 wherein said vector is a viral vector.

4. The vector of claim 3, wherein said vector is a retroviral vector, an adenoassociated viral vector, or an adenoviral vector.

5. A composition comprising the vector of claim 2 and a carrier.

* * * * *

UNITED STATES PATENT AND TRADEMARK OFFICE
CERTIFICATE OF CORRECTION

PATENT NO. : 5,958,893

DATED : Sept. 28, 1999

INVENTOR(S) : Welsh et al.

It is certified that error appears in the above-identified patent and that said Letters Patent is hereby corrected as shown below:

On the title page: Item

[56] References Cited, FOREIGN PATENT DOCUMENTS, line 3: "2037478 4/1991 WIPO" should read --2037478 4/1991 Canada--; OTHER PUBLICATIONS, line 2: "Miller et al. I" should read --Miller et al.-- ;

line 9: insert --Flotte, et al., *The Journal of Biological Chemistry*, Vol. 268, No. 5, pp. 3781-3790, February 15, 1993-- .

IN THE CLAIMS:

Column 25, claim 1, line 52, "SEQ D NO: 1" should read --SEQ ID NO. 1--.

Signed and Sealed this

Thirtieth Day of January, 2001

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2640 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 133..2640

(xi) SEQUENCE DESCRIPTION: SEQ ID NO:1:

```
AATTGGAAGC AAATGACATC ACAGCAGGTC AGAGAAAAAG GGTTGAGCGG CAGGCACCCA      60

GAGTAGTAGG TCTTTGGCAT TAGGAGCTTG AGCCCAGACG GCCCTAGCAG GGACCCCAGC     120

GCCCGAGAGA CC ATG CAG AGG TCG CCT CTG GAA AAG GCC AGC GTT GTC        168
              Met Gln Arg Ser Pro Leu Glu Lys Ala Ser Val Val
                1               5                  10

TCC AAA CTT TTT TTC AGC TGG ACC AGA CCA ATT TTG AGG AAA GGA TAC      216
```

```
                Ser Lys Leu Phe Phe Ser Trp Thr Arg Pro Ile Leu Arg Lys Gly Tyr
                         15                  20                  25

AGA CAG CGC CTG GAA TTG TCA GAC ATA TAC CAA ATC CCT TCT GTT GAT                  264
Arg Gln Arg Leu Glu Leu Ser Asp Ile Tyr Gln Ile Pro Ser Val Asp
         30                  35                  40

TCT GCT GAC AAT CTA TCT GAA AAA TTG GAA AGA GAA TGG GAT AGA GAG                  312
Ser Ala Asp Asn Leu Ser Glu Lys Leu Glu Arg Glu Trp Asp Arg Glu
 45                  50                  55                  60

CTG GCT TCA AAG AAA AAT CCT AAA CTC ATT AAT GCC CTT CGG CGA TGT                  360
Leu Ala Ser Lys Lys Asn Pro Lys Leu Ile Asn Ala Leu Arg Arg Cys
                 65                  70                  75

TTT TTC TGG AGA TTT ATG TTC TAT GGA ATC TTT TTA TAT TTA GGG GAA                  408
Phe Phe Trp Arg Phe Met Phe Tyr Gly Ile Phe Leu Tyr Leu Gly Glu
             80                  85                  90

GTC ACC AAA GCA GTA CAG CCT CTC TTA CTG GGA AGA ATC ATA GCT TCC                  456
Val Thr Lys Ala Val Gln Pro Leu Leu Leu Gly Arg Ile Ile Ala Ser
         95                 100                 105

TAT GAC CCG GAT AAC AAG GAG GAA CGC TCT ATC GCG ATT TAT CTA GGC                  504
Tyr Asp Pro Asp Asn Lys Glu Glu Arg Ser Ile Ala Ile Tyr Leu Gly
    110                 115                 120

ATA GGC TTA TGC CTT CTC TTT ATT GTG AGG ACA CTG CTC CTA CAC CCA                  552
Ile Gly Leu Cys Leu Leu Phe Ile Val Arg Thr Leu Leu Leu His Pro
125                 130                 135                 140

GCC ATT TTT GGC CTT CAT CAC ATT GGA ATG CAG ATG AGA ATA GCT ATG                  600
Ala Ile Phe Gly Leu His His Ile Gly Met Gln Met Arg Ile Ala Met
                145                 150                 155

TTT AGT TTG ATT TAT AAG AAG ACT TTA AAG CTG TCA AGC CGT GTT CTA                  648
Phe Ser Leu Ile Tyr Lys Lys Thr Leu Lys Leu Ser Ser Arg Val Leu
            160                 165                 170

GAT AAA ATA AGT ATT GGA CAA CTT GTT AGT CTC CTT TCC AAC AAC CTG                  696
Asp Lys Ile Ser Ile Gly Gln Leu Val Ser Leu Leu Ser Asn Asn Leu
        175                 180                 185

AAC AAA TTT GAT GAA GGA CTT GCA TTG GCA CAT TTC GTG TGG ATC GCT                  744
Asn Lys Phe Asp Glu Gly Leu Ala Leu Ala His Phe Val Trp Ile Ala
    190                 195                 200

CCT TTG CAA GTG GCA CTC CTC ATG GGG CTA ATC TGG GAG TTG TTA CAG                  792
Pro Leu Gln Val Ala Leu Leu Met Gly Leu Ile Trp Glu Leu Leu Gln
205                 210                 215                 220

GCG TCT GCC TTC TGT GGA CTT GGT TTC CTG ATA GTC CTT GCC CTT TTT                  840
Ala Ser Ala Phe Cys Gly Leu Gly Phe Leu Ile Val Leu Ala Leu Phe
                225                 230                 235

CAG GCT GGG CTA GGG AGA ATG ATG ATG AAG TAC AGA GAT CAG AGA GCT                  888
Gln Ala Gly Leu Gly Arg Met Met Met Lys Tyr Arg Asp Gln Arg Ala
            240                 245                 250

GGG AAG ATC AGT GAA AGA CTT GTG ATT ACC TCA GAA ATG ATT GAA AAT                  936
Gly Lys Ile Ser Glu Arg Leu Val Ile Thr Ser Glu Met Ile Glu Asn
        255                 260                 265

ATC CAA TCT GTT AAG GCA TAC TGC TGG GAA GAA GCA ATG GAA AAA ATG                  984
Ile Gln Ser Val Lys Ala Tyr Cys Trp Glu Glu Ala Met Glu Lys Met
    270                 275                 280

ATT GAA AAC TTA AGA CAA ACA GAA CTG AAA CTG ACT CGG AAG GCA GCC                 1032
Ile Glu Asn Leu Arg Gln Thr Glu Leu Lys Leu Thr Arg Lys Ala Ala
285                 290                 295                 300

TAT GTG AGA TAC TTC AAT AGC TCA GAA TTC TTC TTC TCA GGG TTC TTT                 1080
Tyr Val Arg Tyr Phe Asn Ser Ser Glu Phe Phe Phe Ser Gly Phe Phe
                305                 310                 315

GTG GTG TTT TTA TCT GTG CTT CCC TAT GCA CTA ATC AAA GGA ATC ATC                 1128
Val Val Phe Leu Ser Val Leu Pro Tyr Ala Leu Ile Lys Gly Ile Ile
            320                 325                 330

CTC CGG AAA ATA TTC ACC ACC ATC TCA TTC TGC ATT GTT CTG CGC ATG                 1176
```

```
                Leu Arg Lys Ile Phe Thr Thr Ile Ser Phe Cys Ile Val Leu Arg Met
                        335                 340                 345

GCG GTC ACT CGG CAA TTT CCC TGG GCT GTA CAA ACA TGG TAT GAC TCT         1224
Ala Val Thr Arg Gln Phe Pro Trp Ala Val Gln Thr Trp Tyr Asp Ser
350                 355                 360

CTT GGA GCA ATA AAC AAA ATA CAG GAT TTC TTA CAA AAG CAA GAA TAT         1272
Leu Gly Ala Ile Asn Lys Ile Gln Asp Phe Leu Gln Lys Gln Glu Tyr
365                 370                 375                 380

AAG ACA TTG GAA TAT AAC TTA ACG ACT ACA GAA GTA GTG ATG GAG AAT         1320
Lys Thr Leu Glu Tyr Asn Leu Thr Thr Thr Glu Val Val Met Glu Asn
                        385                 390                 395

GTA ACA GCC TTC TGG GAG GAG GGA TTT GGG GAA TTA TTT GAG AAA GCA         1368
Val Thr Ala Phe Trp Glu Glu Gly Phe Gly Glu Leu Phe Glu Lys Ala
            400                 405                 410

AAA CAA AAC AAT AAC AAT AGA AAA ACT TCT AAT GGT GAT GAC AGC CTC         1416
Lys Gln Asn Asn Asn Asn Arg Lys Thr Ser Asn Gly Asp Asp Ser Leu
                415                 420                 425

TTC TTC AGT AAT TTC TCA CTT CTT GGT ACT CCT GTC CTG AAA GAT ATT         1464
Phe Phe Ser Asn Phe Ser Leu Leu Gly Thr Pro Val Leu Lys Asp Ile
        430                 435                 440

AAT TTC AAG ATA GAA AGA GGA CAG TTG TTG GCG GTT GCT GGA TCC ACT         1512
Asn Phe Lys Ile Glu Arg Gly Gln Leu Leu Ala Val Ala Gly Ser Thr
445                 450                 455                 460

GGA GCA GGC AAG ACT TCA CTT CTA ATG ATG ATT ATG GGA GAA CTG GAG         1560
Gly Ala Gly Lys Thr Ser Leu Leu Met Met Ile Met Gly Glu Leu Glu
                        465                 470                 475

CCT TCA GAG GGT AAA ATT AAG CAC AGT GGA AGA ATT TCA TTC TGT TCT         1608
Pro Ser Glu Gly Lys Ile Lys His Ser Gly Arg Ile Ser Phe Cys Ser
            480                 485                 490

CAG TTT TCC TGG ATT ATG CCT GGC ACC ATT AAA GAA AAT ATC ATC TTT         1656
Gln Phe Ser Trp Ile Met Pro Gly Thr Ile Lys Glu Asn Ile Ile Phe
                495                 500                 505

GGT GTT TCC TAT GAT GAA TAT AGA TAC AGA AGC GTC ATC AAA GCA TGC         1704
Gly Val Ser Tyr Asp Glu Tyr Arg Tyr Arg Ser Val Ile Lys Ala Cys
        510                 515                 520

CAA CTA GAA GAG GAC ATC TCC AAG TTT GCA GAG AAA GAC AAT ATA GTT         1752
Gln Leu Glu Glu Asp Ile Ser Lys Phe Ala Glu Lys Asp Asn Ile Val
525                 530                 535                 540

CTT GGA GAA GGT GGA ATC ACA CTG AGT GGA GGT CAA CGA GCA AGA ATT         1800
Leu Gly Glu Gly Gly Ile Thr Leu Ser Gly Gly Gln Arg Ala Arg Ile
                        545                 550                 555

TCT TTA GCA AGA GCA GTA TAC AAA GAT GCT GAT TTG TAT TTA TTA GAC         1848
Ser Leu Ala Arg Ala Val Tyr Lys Asp Ala Asp Leu Tyr Leu Leu Asp
            560                 565                 570

TCT CCT TTT GGA TAC CTA GAT GTT TTA ACA GAA AAA GAA ATA TTT GAA         1896
Ser Pro Phe Gly Tyr Leu Asp Val Leu Thr Glu Lys Glu Ile Phe Glu
                575                 580                 585

AGC TGT GTC TGT AAA CTG ATG GCT AAC AAA ACT AGG ATT TTG GTC ACT         1944
Ser Cys Val Cys Lys Leu Met Ala Asn Lys Thr Arg Ile Leu Val Thr
        590                 595                 600

TCT AAA ATG GAA CAT TTA AAG AAA GCT GAC AAA ATA TTA ATT TTG CAT         1992
Ser Lys Met Glu His Leu Lys Lys Ala Asp Lys Ile Leu Ile Leu His
605                 610                 615                 620

GAA GGT AGC AGC TAT TTT TAT GGG ACA TTT TCA GAA CTC CAA AAT CTA         2040
Glu Gly Ser Ser Tyr Phe Tyr Gly Thr Phe Ser Glu Leu Gln Asn Leu
                        625                 630                 635

CAG CCA GAC TTT AGC TCA AAA CTC ATG GGA TGT GAT TCT TTC GAC CAA         2088
Gln Pro Asp Phe Ser Ser Lys Leu Met Gly Cys Asp Ser Phe Asp Gln
            640                 645                 650

TTT AGT GCA GAA AGA AGA AAT TCA ATC CTA ACT GAG ACC TTA CAC CGT         2136
```

```
        Phe Ser Ala Glu Arg Arg Asn Ser Ile Leu Thr Glu Thr Leu His Arg
                    655                 660                 665

TTC TCA TTA GAA GGA GAT GCT CCT GTC TCC TGG ACA GAA ACA AAA AAA           2184
Phe Ser Leu Glu Gly Asp Ala Pro Val Ser Trp Thr Glu Thr Lys Lys
        670                 675                 680

CAA TCT TTT AAA CAG ACT GGA GAG TTT GGG GAA AAA AGG AAG AAT TCT           2232
Gln Ser Phe Lys Gln Thr Gly Glu Phe Gly Glu Lys Arg Lys Asn Ser
685                 690                 695                 700

ATT CTC AAT CCA ATC AAC TCT ATA CGA AAA TTT TCC ATT GTG CAA AAG           2280
Ile Leu Asn Pro Ile Asn Ser Ile Arg Lys Phe Ser Ile Val Gln Lys
                    705                 710                 715

ACT CCC TTA CAA ATG AAT GGC ATC GAA GAG GAT TCT GAT GAG CCT TTA           2328
Thr Pro Leu Gln Met Asn Gly Ile Glu Glu Asp Ser Asp Glu Pro Leu
                720                 725                 730

GAG AGA AGG CTG TCC TTA GTA CCA GAT TCT GAG CAG GGA GAG GCG ATA           2376
Glu Arg Arg Leu Ser Leu Val Pro Asp Ser Glu Gln Gly Glu Ala Ile
            735                 740                 745

CTG CCT CGC ATC AGC GTG ATC AGC ACT GGC CCC ACG CTT CAG GCA CGA           2424
Leu Pro Arg Ile Ser Val Ile Ser Thr Gly Pro Thr Leu Gln Ala Arg
        750                 755                 760

AGG AGG CAG TCT GTC CTG AAC CTG ATG ACA CAC TCA GTT AAC CAA GGT           2472
Arg Arg Gln Ser Val Leu Asn Leu Met Thr His Ser Val Asn Gln Gly
765                 770                 775                 780

CAG AAC ATT CAC CGA AAG ACA ACA GCA TCC ACA CGA AAA GTG TCA CTG           2520
Gln Asn Ile His Arg Lys Thr Thr Ala Ser Thr Arg Lys Val Ser Leu
                    785                 790                 795

GCC CCT CAG GCA AAC TTG ACT GAA CTG GAT ATA TAT TCA AGA AGG TTA           2568
Ala Pro Gln Ala Asn Leu Thr Glu Leu Asp Ile Tyr Ser Arg Arg Leu
                800                 805                 810

TCT CAA GAA ACT GGC TTG GAA ATA AGT GAA GAA ATT AAC GAA GAA GAC           2616
Ser Gln Glu Thr Gly Leu Glu Ile Ser Glu Glu Ile Asn Glu Glu Asp
            815                 820                 825

TTA AAG GAG TGC CTT TTT GAT GAT                                           2640
Leu Lys Glu Cys Leu Phe Asp Asp
        830                 835

(2) INFORMATION FOR SEQ ID NO:2:

(i) SEQUENCE CHARACTERISTICS:
        (A) LENGTH: 836 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110
```

-continued

Asn Lys Glu Glu Arg Ser Ile Ala Ile Tyr Leu Gly Ile Gly Leu Cys
    115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
290                 295                 300

Phe Asn Ser Ser Glu Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
        530                 535                 540

```
Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
                580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
        610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Leu Phe Asp Asp
            835
```